United States Patent
Glazier et al.

(10) Patent No.: US 9,339,385 B2
(45) Date of Patent: May 17, 2016

(54) BALLOON RELEASE MECHANISM FOR TAVI IMPLANT

(71) Applicant: St. Jude Medical, Cardiology Division, Inc., St. Paul, MN (US)

(72) Inventors: Valerie J. Glazier, Eden Prairie, MN (US); Huisun Wang, Maple Grove, MN (US); Alex Grafov, Eden Prairie, MN (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 175 days.

(21) Appl. No.: 14/199,029

(22) Filed: Mar. 6, 2014

(65) Prior Publication Data

US 2014/0257457 A1    Sep. 11, 2014

Related U.S. Application Data

(60) Provisional application No. 61/774,021, filed on Mar. 7, 2013.

(51) Int. Cl.
| | |
|---|---|
| *A61F 2/24* | (2006.01) |
| *A61F 2/95* | (2013.01) |
| *A61F 2/958* | (2013.01) |
| *A61F 2/962* | (2013.01) |
| *A61F 2/966* | (2013.01) |
| *A61F 2/91* | (2013.01) |

(52) U.S. Cl.
CPC .............. *A61F 2/2433* (2013.01); *A61F 2/958* (2013.01); *A61F 2/2436* (2013.01); *A61F 2/91* (2013.01); *A61F 2/962* (2013.01); *A61F 2/966* (2013.01); *A61F 2002/9505* (2013.01); *A61F 2002/9583* (2013.01); *A61F 2002/9665* (2013.01)

(58) Field of Classification Search
CPC ...... A61F 2/2433; A61F 2/2427; A61F 2/243; A61F 2/2436; A61F 2/958; A61F 2/95; A61F 2/962; A61F 2/966; A61F 2002/9586; A61F 2002/9665; A61F 2002/9583
See application file for complete search history.

(56) References Cited

U.S. PATENT DOCUMENTS

| | | | | |
|---|---|---|---|---|
| 5,665,103 | A * | 9/1997 | Lafontaine | A61B 5/05 606/192 |
| 5,733,325 | A * | 3/1998 | Robinson | A61F 2/07 623/1.11 |
| 5,824,041 | A * | 10/1998 | Lenker | A61F 2/91 606/195 |
| 6,027,510 | A * | 2/2000 | Alt | A61F 2/958 606/108 |
| 6,091,980 | A * | 7/2000 | Squire | A61F 2/958 600/373 |
| 6,214,036 | B1 * | 4/2001 | Letendre | A61F 2/07 623/1.11 |
| 6,695,809 | B1 * | 2/2004 | Lee | A61F 2/958 604/96.01 |

(Continued)

*Primary Examiner* — Christopher L Templeton
(74) *Attorney, Agent, or Firm* — Lerner, David, Littenberg, Krumholz & Mentlik, LLP (57) ABSTRACT

A delivery system for an implantable medical device having at least one retention member at an end thereof includes a shaft extending in a longitudinal direction. An elongated sheath surrounds the shaft. The sheath is slidable relative to the shaft in the longitudinal direction. A space is defined inside of the sheath and is adapted to receive the medical device in an assembled or collapsed condition. A retainer is positioned at a first end of the space. At least one recess is provided in the retainer and is adapted to receive the retention member of the medical device in the assembled condition. A selectively activatable member is disposed in the compartment between the longitudinal shaft and the medical device. When in an activated state, the member expands radially relative to the shaft, thereby urging the retention member to disengage from the recess.

13 Claims, 9 Drawing Sheets

(56) References Cited

U.S. PATENT DOCUMENTS

| | | | | |
|---|---|---|---|---|
| 6,858,034 B1* | 2/2005 | Hijlkema | A61F 2/95 | 606/108 |
| 8,147,541 B2* | 4/2012 | Forster | A61F 2/2439 | 623/2.11 |
| 8,414,640 B2* | 4/2013 | Schmitt | A61F 2/95 | 623/1.23 |
| 9,138,315 B2* | 9/2015 | Straubinger | A61F 2/2427 | |
| 2002/0055767 A1* | 5/2002 | Forde | A61B 17/0057 | 623/1.11 |
| 2002/0193868 A1* | 12/2002 | Mitelberg | A61F 2/91 | 623/1.15 |
| 2004/0087900 A1* | 5/2004 | Thompson | A61F 2/91 | 604/96.01 |
| 2004/0093063 A1* | 5/2004 | Wright | A61F 2/95 | 623/1.12 |
| 2004/0204749 A1* | 10/2004 | Gunderson | A61F 2/91 | 623/1.12 |
| 2004/0267348 A1* | 12/2004 | Gunderson | A61F 2/91 | 623/1.12 |
| 2006/0276872 A1* | 12/2006 | Arbefeuille | A61F 2/07 | 623/1.11 |
| 2007/0293930 A1* | 12/2007 | Wang | A61F 2/91 | 623/1.11 |
| 2008/0114443 A1* | 5/2008 | Mitchell | A61F 2/07 | 623/1.13 |
| 2008/0228255 A1* | 9/2008 | Rust | A61M 25/0147 | 623/1.11 |
| 2008/0255655 A1* | 10/2008 | Kusleika | A61F 2/91 | 623/1.11 |
| 2008/0262590 A1* | 10/2008 | Murray | A61F 2/95 | 623/1.11 |
| 2008/0264102 A1* | 10/2008 | Berra | A61F 2/07 | 63/1.11 |
| 2009/0276027 A1* | 11/2009 | Glynn | A61F 2/95 | 623/1.11 |
| 2009/0287290 A1* | 11/2009 | Macaulay | A61F 2/2412 | 623/1.11 |
| 2010/0010612 A1* | 1/2010 | Gelbart | A61F 2/958 | 623/1.11 |
| 2010/0268315 A1* | 10/2010 | Glynn | A61F 2/95 | 623/1.11 |
| 2011/0098805 A1* | 4/2011 | Dwork | A61F 2/2436 | 623/2.11 |
| 2011/0245917 A1* | 10/2011 | Savage | A61F 2/2427 | 623/2.11 |
| 2011/0251666 A1* | 10/2011 | Schmitt | A61F 2/95 | 623/1.11 |
| 2011/0251682 A1* | 10/2011 | Murray, III | A61F 2/2436 | 623/2.11 |
| 2011/0257720 A1* | 10/2011 | Peterson | A61F 2/95 | 623/1.11 |
| 2011/0264202 A1* | 10/2011 | Murray, III | A61F 2/2418 | 623/2.11 |
| 2011/0301702 A1* | 12/2011 | Rust | A61F 2/2418 | 623/2.11 |
| 2013/0204344 A1* | 8/2013 | Tatalovich | A61F 2/962 | 623/1.12 |
| 2014/0364942 A1* | 12/2014 | Straubinger | A61F 2/2436 | 623/2.11 |

* cited by examiner

FIG. 6C

BALLOON RELEASE MECHANISM FOR TAVI IMPLANT

CROSS-REFERENCE TO RELATED APPLICATIONS

The present application claims the benefit of the filing date of the U.S. Provisional Patent Application No. 61/774,021, filed on Mar. 7, 2013, the disclosure of which application is hereby incorporated by reference in its entirety.

BACKGROUND OF THE INVENTION

The present disclosure is related to heart valve repair, and more particularly to devices, systems, and methods for Transcatheter Aortic-Valve Implantation (TAVI).

Prosthetic heart valves that are collapsible to a relatively small circumferential size can be delivered into a patient less invasively than valves that are not collapsible. For example, a collapsible valve may be delivered into a patient via a tube-like delivery apparatus such as a catheter, a trocar, a laparoscopic instrument, or the like. This collapsibility can avoid the need for a more invasive procedure such as full open-chest, open-heart surgery.

Collapsible prosthetic heart valves typically take the form of a valve structure mounted on a stent. There are two types of stents on which collapsible valves are mounted: a self-expanding stent and a balloon-expandable stent. To place a collapsible valve into a delivery apparatus and ultimately into a patient, the valve must first be collapsed or crimped to reduce its circumferential size.

When a collapsed valve has reached the desired implant site in the patient (e.g., at or near the annulus of the patient's heart valve that is to be replaced by the prosthetic valve), the prosthetic valve can be released from the delivery apparatus and re-expanded to full operating size.

BRIEF SUMMARY OF THE INVENTION

According to an embodiment of the disclosure, a delivery system for an implantable medical device having at least one retention member at an end thereof comprises a shaft extending in a longitudinal direction. An elongated sheath surrounds the shaft. The sheath is slidable relative to the shaft in the longitudinal direction. A medical device receiving space is defined inside of the sheath and is adapted to receive the medical device in an assembled or collapsed condition. A retainer is positioned at a first end of the space. At least one recess is provided in the retainer and is adapted to receive the retention member of the medical device in the assembled condition. A selectively activable member is disposed in the space between the longitudinal shaft and the medical device. When in an activated state, the member expands radially relative to the shaft, thereby urging the retention member to disengage from the recess.

According to an embodiment of the disclosure, a delivery system for an implantable medical device comprises an implantable device having at least one retention member and a delivery device for releasably securing the implantable device thereto. The delivery device comprises an elongated shaft, an elongated sheath surrounding a portion of the shaft and slidable relative thereto in a longitudinal direction and retainer coupled to the shaft and configured to be received within the sheath. The retainer has a portion thereof configured to releasably receive the at least one retention member of the implantable device. The delivery device further comprises a selectively inflatable member adapted to be disposed in a space between the shaft and the implantable device. The at least one retention member is configured to be released upon inflation of the inflatable member.

According to an aspect of the disclosure, a method for delivering an implantable medical device having at least one retention member coupled to a stent thereof comprises positioning a delivery device comprising a retainer, and the medical device, and a balloon element disposed underneath at least the stent, at a predetermined location in a heart. The implantable medical device is in a collapsed state thereof with the retention member engaged with corresponding at least one recess in the retainer. The method further comprises unsheathing the space to expose at least the stent portion of the implantable medical device. If one or more of the at least one retention member remain engaged with one or more of the corresponding recesses, the method further comprises causing the balloon element to expand to disengage the one or more of the at least one retention member from the one or more of the corresponding recesses in the retainer.

BRIEF DESCRIPTION OF THE DRAWINGS

Various embodiments of the present disclosure will now be discussed with reference to the appended drawings. It is to be appreciated that these drawings depict only some embodiments of the disclosure and are therefore not to be considered limiting of its scope.

DETAILED DESCRIPTION

Despite the various improvements that have been made to the collapsible prosthetic heart valve delivery process, conventional delivery devices, systems, and methods suffer from some shortcomings. For example, the self expanding collapsible valve may be held in a catheter by stent retention members that are inserted into the retainer portion of the catheter. During deployment of the self expanding valve into the desired area (e.g., the aortic valve annulus), the high frictional force produced during unsheathing of the valve may cause high axial forces to be applied directly to the two or three retention members, which may damage or deform the stent struts that support the retention members.

Furthermore, the delivery process may cause the stent to become twisted relative to the retainer portion of the catheter, which may make it difficult to release the valve because the stent retention members may catch on the retainer during deployment.

There therefore is a need for further improvements to the devices, systems, and methods for transcatheter delivery of collapsible prosthetic heart valves. Among other advantages, the present disclosure may address one or more of these shortcomings.

As used herein, the terms "proximal" and "distal" are to be taken as relative to a user (e.g., a surgeon or an interventional cardiologist) using the disclosed transcatheter devices. "Proximal" is to be understood as relatively close to the user and "distal" is to be understood as relatively farther away from the user. The various embodiments will be described in connection with the repair of a mitral valve leaflet, but it may be useful in the repair of other types of cardiac valves or in the gathering and clamping of other types of loose body tissue.

Figure 1A:
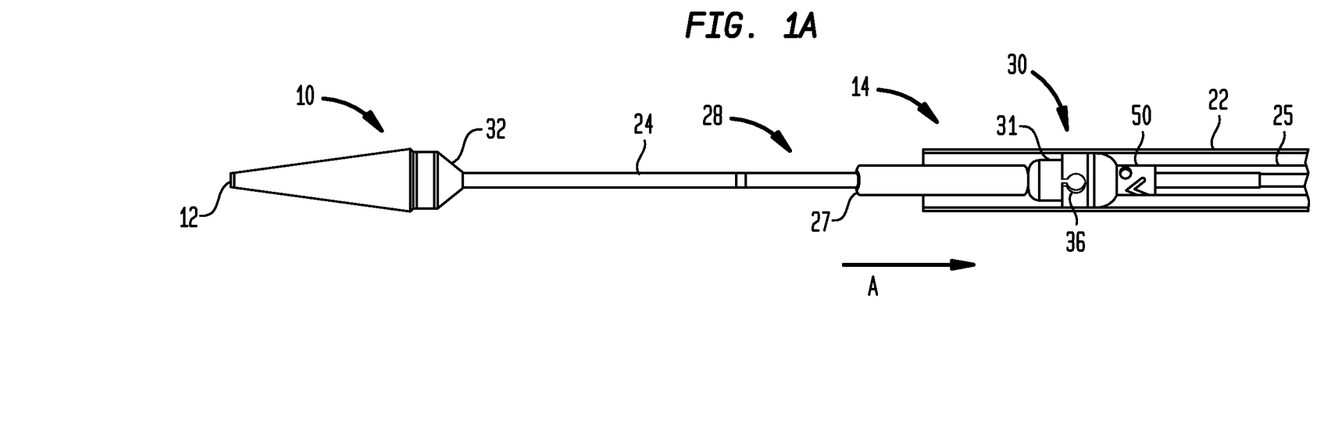
FIG. 1A is a side view in partial cross-section of a transfemoral delivery device for a collapsible prosthetic heart valve, schematically illustrating the balloon element in a deflated condition, according to an embodiment of the disclosure.
Figure 1B:
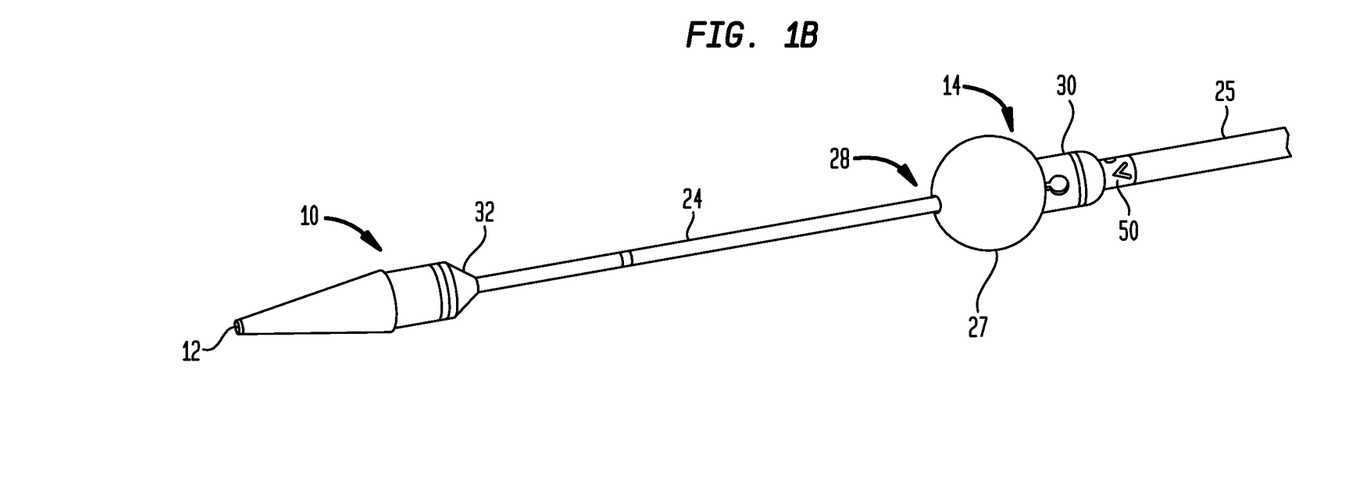
FIG. 1B is a perspective view of the delivery device of FIG. 1A, schematically illustrating the balloon element in an expanded condition, according to an embodiment of the disclosure.
Figure 1C:
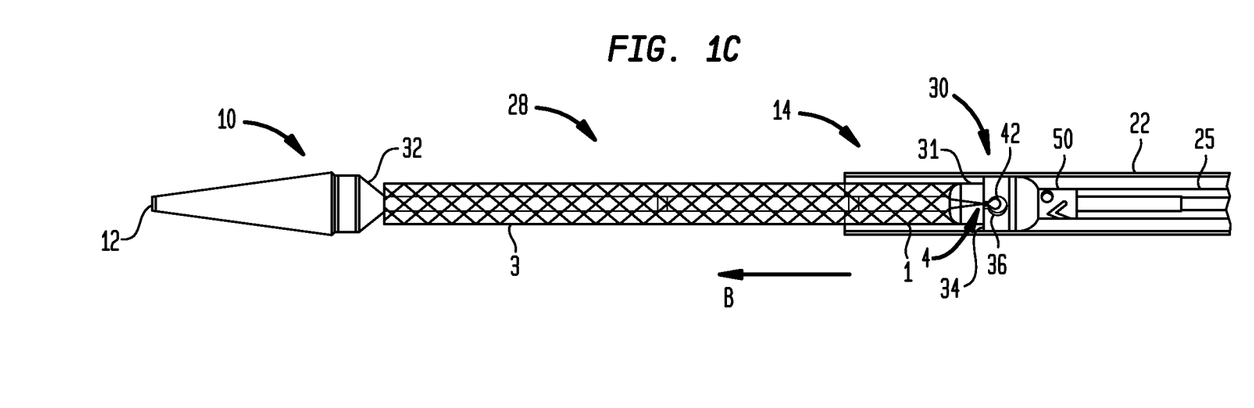
FIG. 1C is a side view of the device of FIG. 1A, schematically illustrating a collapsible prosthetic heart valve in a collapsed condition coupled to a retainer, according to an embodiment of the disclosure.

Referring now to FIGS. 1A-1C illustrating an embodiment of the disclosure, delivery device 10 has distal tip 12 and catheter assembly 14 extending from the distal tip to a proximal end (not shown) that includes a handle (not shown) for a user to control the delivery device. Delivery device 10 is an exemplary transfemoral delivery device for collapsible prosthetic heart valve 3.

Although delivery device 10 is a transfemoral delivery device, the retainers shown and described in this application may be configured to be used with a transapical delivery device (e.g., device 10' shown in FIGS. 6A and 6B) or other types of tube-like delivery devices for collapsible stents.

Catheter assembly 14 includes sheath 22 extending from the handle towards distal tip 12, inner shaft 24 located inside of the sheath and extending from the handle to the distal tip, and valve receiving space 28 configured to receive prosthetic valve 3 for delivery inside of a patient.

Valve receiving space 28 is configured to receive self-expanding collapsible prosthetic heart valve 3 therewithin and is delimited by proximal conical body 31 adjacent to retainer 30 located inside sheath 22 on one end, and distal conical body 32 spaced distally from the retainer at the other end. Distal conical body 32 is joined to inner shaft 24 at one end of valve receiving space 28, and proximal conical body 31 and retainer 30 are joined to stiffening member 25 mounted on inner shaft 24 at the other end of the valve receiving space. Preferably, inner shaft 24 and stiffening member 25 have defined therein a bore (not shown) having an internal diameter adapted to receive a guide wire (not shown) therewithin. Alternatively, in any of the delivery device embodiments described herein, inner shaft 24 and stiffening member 25 may be a single unitary shaft. For delivery into a patient, self-expanding prosthetic collapsible valve 3 is loaded into valve receiving space 28 around inner shaft 24 and between conical bodies 31 and 32, and stent portion 1 of prosthetic valve 3 is coupled to retainer 30 via one or more retention members 4 extending from the stent portion and corresponding recesses 36 defined along edge 34 of the retainer.

Expandable balloon element 27 is disposed on inner shaft 24 proximal to conical body 31. In FIG. 1A, balloon element 27 is schematically illustrated in a collapsed condition. When in the collapsed condition, balloon element 27 is configured to be encompassed by prosthetic valve 3 in a collapsed condition. The outer dimensions of collapsed balloon element 27 are smaller than or equal to the inner dimensions of collapsed prosthetic heart valve 3 disposed in valve receiving space 28. For clarity of the illustration, the collapsible prosthetic heart valve is not shown in FIG. 1A. Arrow A illustrates the direction of movement of sheath 22 to unsheathe a prosthetic heart valve placed in space 28. Thus, sheath 22 is moved proximally or away from distal tip 12 to unsheathe prosthetic heart valve 3 placed in space 28.

In FIG. 1B, delivery device 10 is illustrated in a perspective view without the self-expanding collapsible valve mounted in valve receiving space 28 or sheath 22 for clarity of the illustration. Expandable balloon element 27 is illustrated in an expanded configuration in valve receiving space 28. As is schematically illustrated, when expanded, balloon element 27 expands to a diameter greater than the outer diameter of retainer 30 generally corresponding to the inner diameter of stent portion 1 of prosthetic heart valve 3 (FIG. 1C). As will be described in more detail later, the selective expansion of expandable balloon element 27 is configured to assist self-expanding stent 1 of collapsible prosthetic heart valve 3 to expand, if necessary, by disengaging retainer members 4 of stent 1 from recesses 36 of retainer 30.

Referring now to FIG. 1C, collapsible prosthetic heart valve 3 is disposed about inner shaft 24 in valve receiving space 28 and is illustrated in a collapsed or compressed condition. In an exemplary embodiment, valve 3 may be collapsed by sheath 22. Balloon element 27 is not illustrated in FIG. 1C for clarity of the illustration. In the collapsed condition, the outer diameter of prosthetic valve 3 is smaller than the inner diameter of sheath 22. Arrow B depicts the direction of movement of sheath 22 to sheathe prosthetic heart valve 3 disposed in valve receiving space 28. Stent portion 1 of prosthetic valve 3 is proximal to and supported by proximal conical body 31. Conical body 31 has an outer diameter which corresponds to the desired inner diameter of stent portion 1 of prosthetic valve 3 in a collapsed or compressed condition.

Figure 1D:
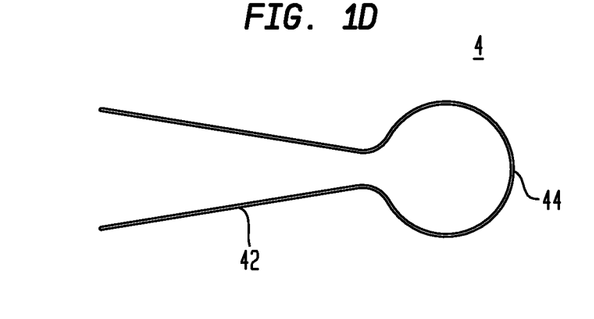
FIG. 1D illustrates a retention member of the stent portion of the prosthetic valve, according to an embodiment of the disclosure.

At least one retention member 4 (FIG. 1D) extends from prosthetic valve 3 proximally beyond proximal conical body 31. In the exemplary embodiment, retention member 4 comprises disc-like end 44 extending from strut 42. Strut 42 extends from stent portion 1 of prosthetic heart valve 3. One or more recesses 36 are defined along edge 34 of retainer 30 (FIG. 1C). Each recess 36 is located at edge 34 of retainer 30 and is configured to receive and engage a corresponding retention member 4 of stent portion 1 of collapsible prosthetic valve 3 when the prosthetic valve is in a collapsed condition. In an exemplary embodiment, each recess 36 preferably has a similar shape and a slightly larger size than stent retention member 4 so as to capture the same readily, but with only a small amount of relief therebetween to substantially restrict the movement of retention member 4 once accommodated therewithin. Thus, forming recess 36 with an appropriate shape and size substantially prevents longitudinal movement of prosthetic valve 3 within valve receiving space 28, such as during deployment or resheathing procedures.

Edge 34 of retainer 30 may have a chamfered outer edge, which may help reduce frictional forces acting between sheath 22 and the retainer during unsheathing and resheathing of stent 1 of prosthetic valve 3. Edge 34 of any of the retainer embodiments disclosed herein may have chamfered outer edges.

Figure 1E:
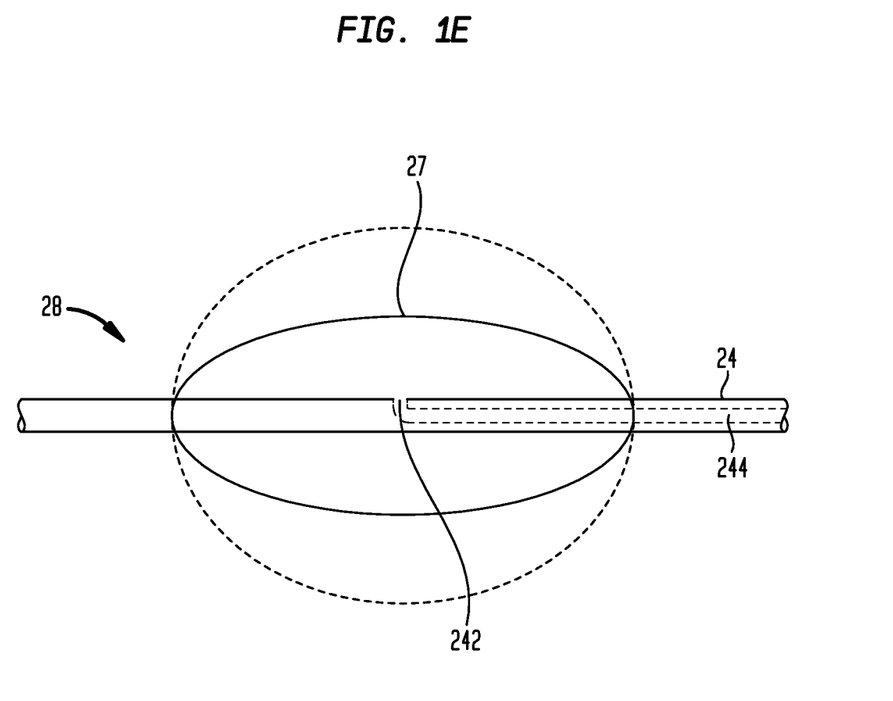
FIG. 1E schematically illustrates the inflatable balloon element according to an embodiment of the disclosure.

Now referring to FIG. 1E, a schematic cross-section of expandable balloon element 27 and a partial view of heart valve receiving space 28 is illustrated, without prosthetic valve 3 or retainer 30 (FIG. 1A). An expanded configuration of expandable balloon element 27 is illustrated in phantom. In an exemplary embodiment, one or more inflation ports 242 are provided in inner shaft 24 for selectively introducing the inflation medium into expandable balloon element 27. An inflation medium may flow through lumen 244 in inner shaft 24 and enter balloon element 27 through one or more inflation ports 242. If expandable balloon element 27 is made of a gas-permeable material, the inflation medium may diffuse through the gas-permeable material. If, on the other hand, balloon element 27 is not made of a gas-permeable material, the inflation medium may be vacuumed from expandable balloon element 27, to remove the inflation medium therefrom, through one or more inflation ports 242 and lumen 244 in inner shaft 24. Further still, in an exemplary embodiment, the inflation medium may be vented to atmosphere through port 242 by venting the opposing end of lumen 244 to the atmosphere.

In an exemplary embodiment, balloon element 27 may be made of an expandable or stretchable material. In one configuration, the material of expandable balloon element 27 is a gas-permeable material, for example, a woven or braided polymer. In other embodiments, expandable balloon element 27 made of other materials such as polyester or rubber. Expandable balloon element 27 is configured to expand upon the entry of the inflation medium through lumen 244 and inflation port 242 in shaft 24. In an exemplary embodiment, the inflation medium may include a liquid such as a saline or a gas such as air or helium. The inflation medium may be selectively caused to expand balloon element 27 by the user, if one or more retention members 4 of stent portion 1 of prosthetic valve 3 remains engaged with recess 36, in spite of self-expansion of the prosthetic heart valve after being unsheathed by sheath 22.

Figure 2A:
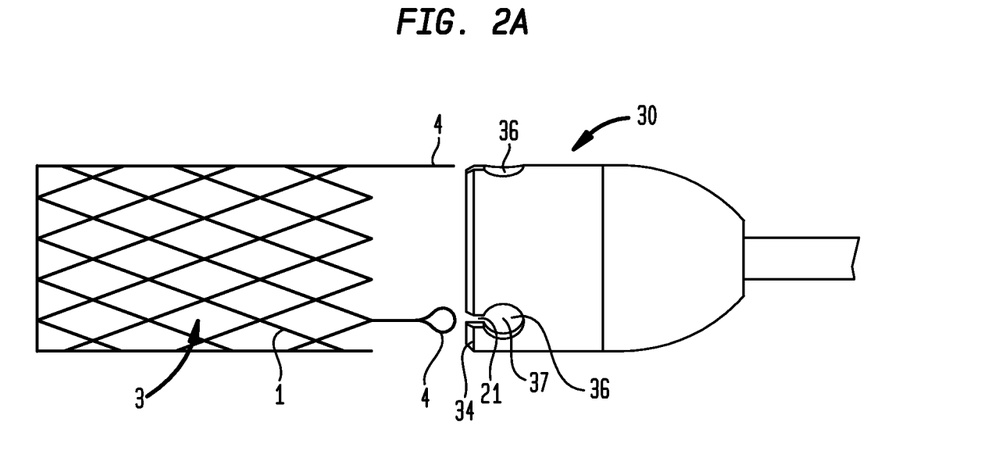
FIG. 2A schematically illustrates an exploded view of the stent portion of the prosthetic valve and the retainer of FIG. 1C.
Figure 2B:
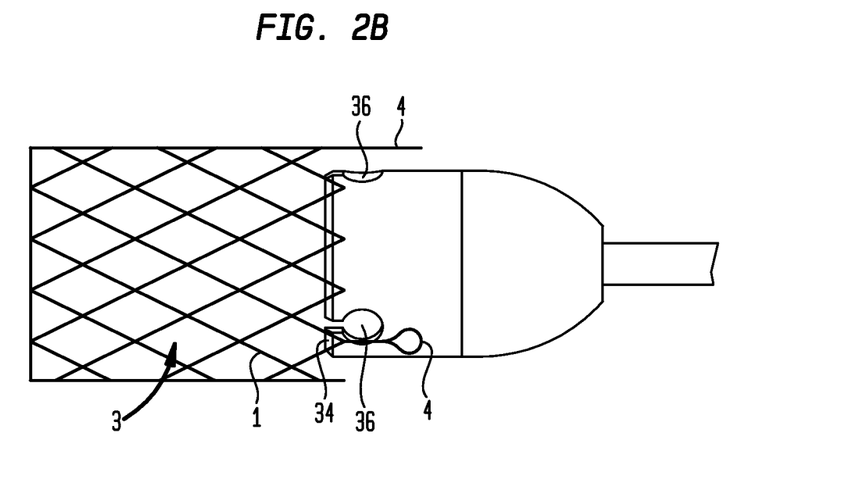
FIG. 2B schematically illustrates the stent portion of FIG. 2A in an expanded configuration prior to engagement of the prosthetic valve with the retainer.
Figure 2C:
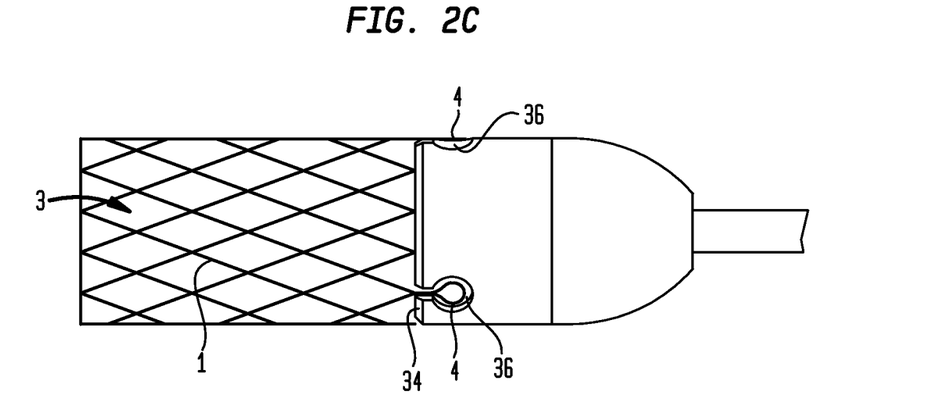
FIG. 2C schematically illustrates retention member of the prosthetic valve of FIG. 2A engaged with the retainer of FIG. 2A, according to an embodiment of the disclosure.

Referring now to FIGS. 2A-2C, a process for engaging retention members 4 of stent portion 1 of prosthetic heart valve 3 (FIG. 1C) to retainer 30 will be described. FIG. 2A schematically illustrates an exploded view of two retention members 4 extending proximally from stent portion 1 of prosthetic valve 3 and two corresponding recesses 36 defined along distal edge 34 of retainer 30. In the compressed condition of prosthetic valve 3, retention members 4 engage corresponding recesses 36 in retainer 30. In an exemplary embodiment, retainer 30 includes sensor 37. Sensor 37 may be configured to detect engagement of retention member 4 of stent portion 1 with corresponding recess 36. Such sensor 37 may be useful in detecting any engagement of retention member 4 with corresponding recess 36, particularly when prosthetic valve 3 has been unsheathed and stent 1 thereof is supposed to expand, thereby disengaging retention member 4 from corresponding recess 36. As shown in FIG. 2B, prosthetic valve 3 is in an expanded condition, when distal tip 12 (FIG. 1A) is inserted through the valve to position retention members 4 in generally proximity of recesses 36. Prosthetic valve 3 is then compressed or crimped, for example, by sheath 22, while ensuring that retention members 4 engage corresponding recesses 36 in retainer 30. Finally, as seen in FIG. 2C, in the compressed condition of prosthetic heart valve 3, retention members 4 are substantially engaged with recesses 36 such that longitudinal movement of valve 3 relative to retainer 30 is substantially restricted. In particular, neck 21 of recess 36, being substantially smaller than disc-like end 42 of retention member 4, substantially restricts the longitudinal movement of retention member 4 relative to retainer 30, and thereby that of prosthetic valve 3, relative to the retainer.

Figure 3A:
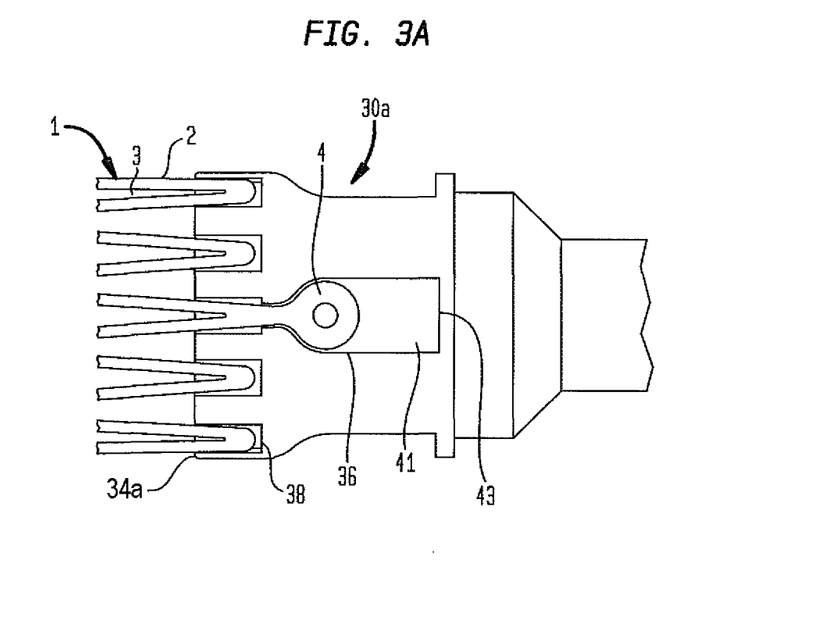
FIG. 3A illustrates another embodiment of a stent portion of the prosthetic heart valve engaged with another embodiment of the retainer.
Figure 3B:
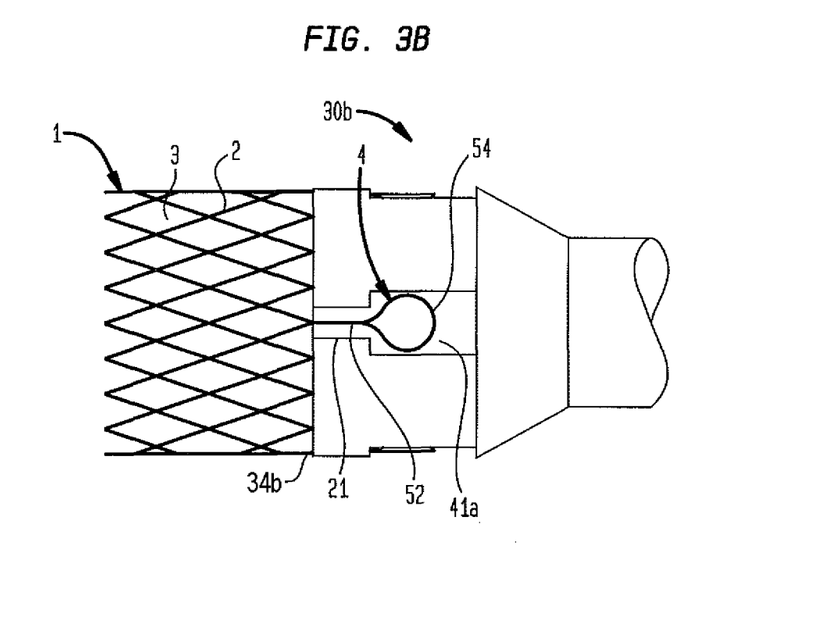
FIG. 3B illustrates yet another embodiment of a stent portion of the prosthetic heart valve engaged with yet another embodiment of the retainer.

Referring to FIGS. 3A-3B, two other exemplary embodiments of retainers and corresponding retention members are schematically illustrated. Retention member 4a is lodged in recess 36a such that the longitudinal movement of prosthetic heart valve 3 relative to retainer 30a is substantially restricted. In addition to recesses 36a, one or more recesses 38 extending inwardly from edge 34a are defined along edge 34a. Recesses 38 are configured to receive the V-shaped junction formed by struts 2 at the end of stent 1. Recesses 38 restrict the longitudinal movement of corresponding stent strut 2 relative to edge 34a. Furthermore, recesses 38 fix the circumferential positions of stent struts 2, preventing them from overlapping with one another and becoming otherwise entangled during the delivery and deployment of prosthetic valve 3.

With prosthetic valve 3 assembled to retainer 30a, as shown in FIG. 3A, retention members 4a of stent portion 1 will be spaced from end wall 43 of pocket 41 of recess 36a. However, should any longitudinal force develop tending to push prosthetic valve 3 against retainer 30a, the engagement of stent struts 2 in recesses 38 will prevent the longitudinal movement of prosthetic valve 3 relative to the retainer. As a result, retention members 4a will remain spaced from end walls 43 of pockets 41, and the compressive force between stent portion 1 and retainer 30a will not be localized at the retention members, but rather will be distributed substantially uniformly around the circumference of stent through stent struts 2. In consideration of the foregoing, it will be appreciated that recesses 38 may be generally U-shaped as shown in FIG. 3A, or may have any other shape that can receive corresponding stent strut 2 and serve the purposes just described.

In the embodiment illustrated in FIG. 3B, edge 34b serves to restrict the longitudinal movement of struts 2. Retention member 4b of FIG. 3B comprises generally linear section 52 extending through neck 21b and loop 54 extending from linear section 52 and configured to engage recess 36b. Loop 54 is sufficiently strong to resist a longitudinal force urging the loop against neck 21b, thereby restricting a proximal longitudinal movement of prosthetic valve 3 relative to retainer 30b.

Figure 4:
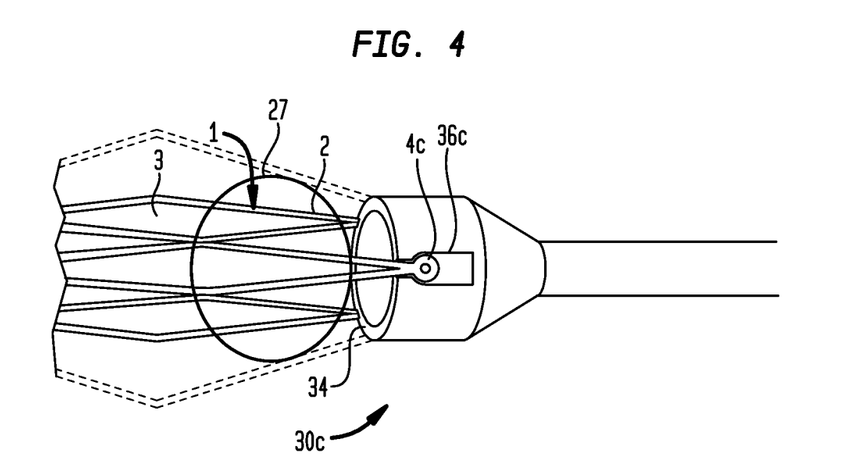
FIG. 4 illustrates schematically the balloon element in an expanded condition for disengaging an embodiment of the retention member of the stent portion from an embodiment of the retainer.

When delivery device 10 (FIGS. 1A-1C) is being used to deliver a collapsible valve into a patient, prosthetic valve 3 may become cocked at an angle relative to retainer 30 and recesses 36 thereof, for example, and may not readily release therefrom when unsheathed by sheath 22. According to an embodiment of the disclosure, balloon element 27 may be selectively inflated causing stent portion 1 of prosthetic valve 3 to expand, as illustrated in FIG. 4. Such an expansion of stent portion 1 would facilitate disengagement of retention members 4c of stent portion 1 from recesses 36c of retainer 30c. Retainer 4c is generally similar to retainer 4a and recesses 36c are generally similar to recesses 36a. Stent 1 illustrated in solid lines depict a collapsed condition of the stent. FIG. 4 schematically illustrates stent 1 in phantom in an expanded condition caused by the inflation of underlying balloon element 27. As underlying balloon element 27 expands radially, the balloon element urges against stent 1 radially outwardly, thereby exerting a radially outward force upon retention member 4c. Such an expansion of balloon element 27 assists in disengaging retention member 4c from recess 36c, in the case if the retention members inadvertently remains engaged with the recess and interferes with the self-expansion of stent 1.

Figure 5:
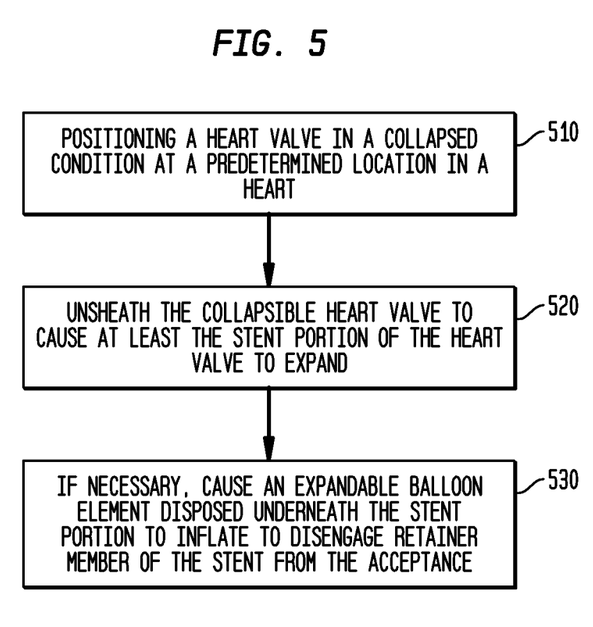
FIG. 5 illustrates a flow diagram for a method for delivering an implantable medical device having at least one retention member at an end thereof engaged with the retainer, according to an aspect of the disclosure.

Referring to FIG. 5, a flow diagram for using delivery device 10 (FIGS. 1A-1C) is illustrated according to an embodiment of the disclosure. With reference to FIGS. 1A-1C, at block 510, collapsible prosthetic heart valve disposed in valve receiving space 28 is positioned at a predetermined location in a heart. Expandable balloon element 27 is disposed underneath at least stent portion 1 of prosthetic heart valve 3 in a collapsed condition. At least one retention member 4 of prosthetic heart valve 3 engages at least one corresponding recess 36. At block 520, sheath 22 from the closed position adjacent distal conical body 22 is moved away from valve receiving space 28, thereby unsheathing prosthetic heart valve 3 and causing at least stent portion 1 of self-expanding prosthetic valve 3 to expand. Ideally, at least one retention member 4 disengages from corresponding at least one recess 36 upon the expansion of prosthetic heart valve 3 into an expanded configuration. However, if one or more retention members 4 remain engaged with corresponding one or more recesses 36, at block 530, expandable balloon element 27 is selectively inflated. The inflation of balloon element 27 exerts a force on stent portion 1 of valve 3 sufficient to cause disengagement of one or more retention member 4 from corresponding one or more recesses 36.

In one configuration, the user may activate the inflation of expandable balloon element 27 if one or more retention members 4 of stent portion 1 of prosthetic heart valve 3 remain inadvertently engaged with corresponding recesses 36. In another embodiment, the inflation of expandable balloon element 27 may be initiated responsive to a sensor 37 sensing a continued engagement of one or more retention members 4 of stent portion 1 with corresponding recess 36 after sheath 22 has uncovered collapsible prosthetic heart valve 3 and the prosthetic valve has self-expanded. If all of retention members 4 of stent portion 1 of collapsible prosthetic heart valve 3 disengage from corresponding recesses 36, then expandable balloon 27 may not need to be inflated.

Figure 6A:
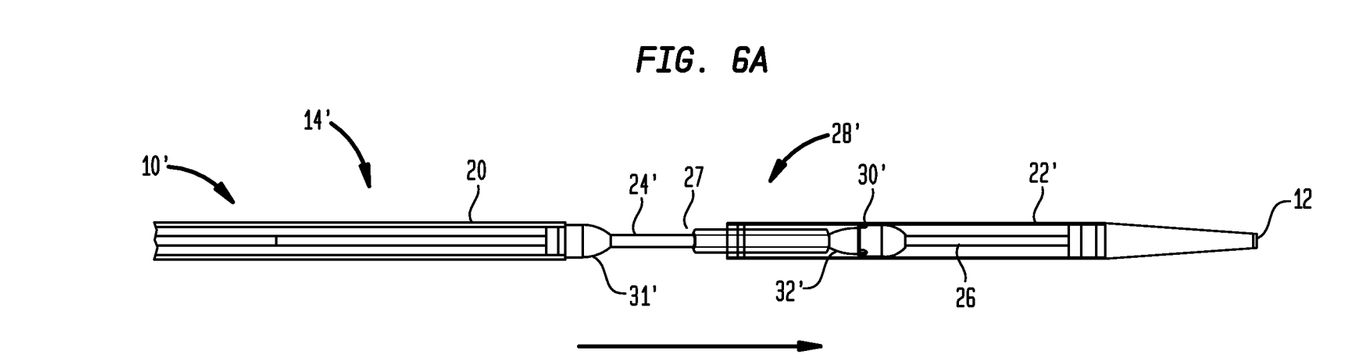
FIG. 6A is a side view in partial cross-section of a transapical delivery device for a collapsible prosthetic heart valve schematically illustrating the balloon element in a deflated condition, according to an embodiment of the disclosure.
Figure 6B:
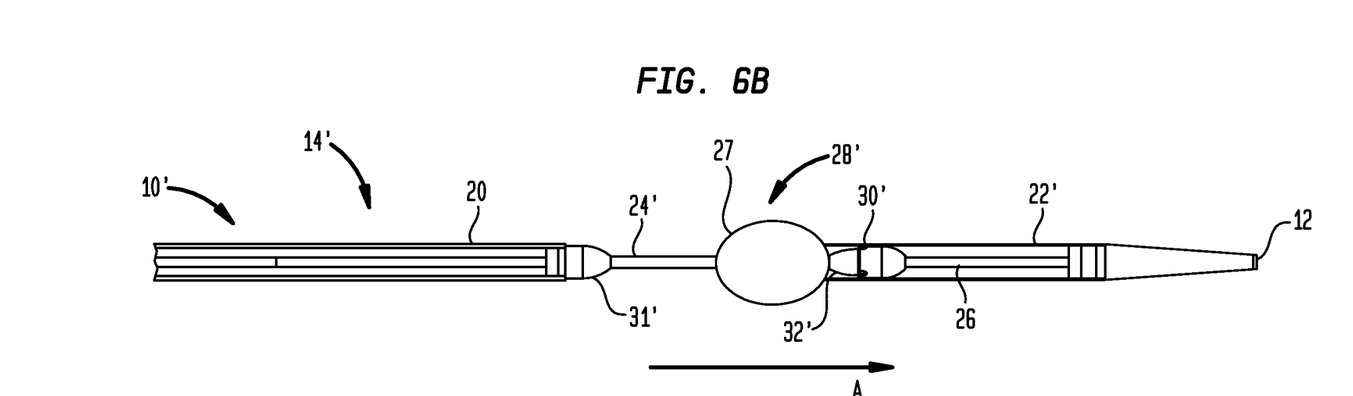
FIG. 6B is a side view in partial cross-section of the transapical delivery device of FIG. 6A, schematically illustrating the balloon element in an expanded condition, according to an embodiment of the disclosure.

Referring to FIGS. 6A-6B, an exemplary embodiment of the disclosure for transapical delivery of a prosthetic collapsible heart valve is illustrated. The delivery device 10' has distal tip 12 and catheter assembly 14' extending from the distal tip to a proximal end (not shown) that includes a handle (not shown) for a user to control the delivery device.

Catheter assembly 14' includes proximal sheath 20 extending from the handle towards distal tip 12, distal sheath 22' extending from the distal tip towards the handle (not shown), hollow tube 26 that extends slidably from the proximal end through the proximal sheath and attaches to the distal sheath at the distal tip of the delivery device, and valve receiving space 28' configured to receive a prosthetic valve for delivery inside of a patient.

Valve receiving space 28' is configured to receive collapsible prosthetic heart valve 3 (not shown, but similar to one illustrated in FIG. 1C) and comprises expandable balloon element 27. In the illustrated embodiment, stent portion 1 of prosthetic valve 3 is disposed proximally relative to distal tip 12, whereas the same is disposed distally relative to distal tip 12 in the embodiment of FIGS. 1A-1C. Valve receiving space 28' includes proximal conical body 31' at the distal end of proximal sheath 20, distal conical body 32' spaced from the proximal conical body, and retainer 30' located adjacent the distal conical body and inside the distal sheath. Expandable balloon element 27 is disposed adjacent to distal conical body 32' and is schematically illustrated in a collapsed configuration. Inner shaft 24' is connected at one end to proximal conical body 31' and at the other end to distal conical body 32', and slidably receives tube 26 therethrough. For delivery into a patient, collapsible valve 3 (FIG. 1C) is loaded into valve receiving space 28' around inner shaft 24' and between conical bodies 31' and 32', and stent portion 1 of valve 3 is coupled to retainer 30'. FIG. 6B illustrates the expanded configuration of expandable balloon element 27. The outer diameter of expanded balloon element 27 is greater than the inner diameter of sheath 22' and generally corresponds to an inner diameter of expanded prosthetic valve 3, as described above with respect to the transfemoral device of FIGS. 1A-1C.

Figure 6C:
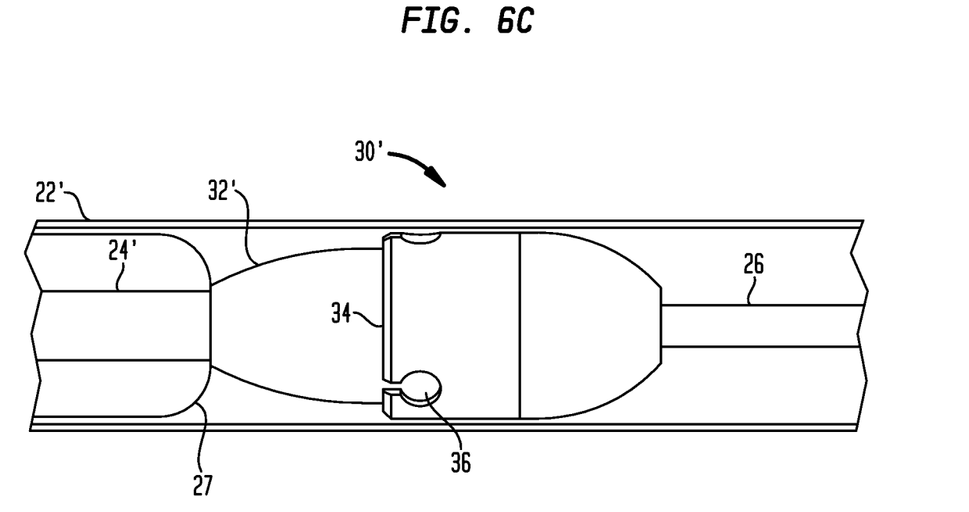
FIG. 6C is a longitudinal side view in a partial cross-section of the retainer of the delivery device depicted in FIG. 6A, shown without the proximal conical and the proximal sheath end.

Referring now to FIG. 6C, retainer 30' includes edge 34. One or more recesses 36 are defined along edge 34 and are configured to receive corresponding retention members 4 (FIG. 1C) of stent portion 1 of collapsible prosthetic valve 3 (FIG. 1C). Each recess 36 preferably has a similar shape and a slightly larger size than stent retention member 4 so as to capture same readily, but with only a small amount of relief therebetween, for substantially restricting the longitudinal movement of prosthetic valve 3 relative to retainer 30'.

In a transapical prosthetic aortic valve delivery device (e.g., the device 10' shown in FIGS. 6A and 6B), edge 34 is located at the proximal end of retainer 30', and distal sheath 22' is moved in a distal direction depicted by the arrow A to unsheathe and deploy prosthetic valve 3, with the proximal end of the prosthetic valve unsheathed first. FIG. 6B illustrates the condition when distal sheath 22' has been moved in a distal direction depicted by the arrow A to unsheathe and deploy prosthetic valve 3. If one or more retention members 4 of stent portion 1 of prosthetic valve 3 are still engaged with one or more corresponding recesses 36, expandable balloon element 27 may be inflated to disengage one or more retention members 4 of stent 1 of prosthetic heart valve 3 from one or more corresponding recesses 36, as described above with regard to transfemoral device 10.

Although the present disclosure has described particular embodiments, it is to be understood that these embodiments are merely illustrative of the principles and applications of the present disclosure. It is therefore to be understood that numerous modifications may be made to the illustrative embodiments and that other arrangements may be devised without departing from the spirit and scope of the present claims.

A delivery system for an implantable medical device having at least one retention member comprises a shaft extending in a longitudinal direction, an elongated sheath surrounding the shaft, the sheath being slidable relative to the shaft in the longitudinal direction, a space defined inside of the sheath and adapted to receive the medical device in an assembled condition, a retainer positioned at a first end of the space, the retainer having at least one recess adapted to receive the retention member of the medical device in the assembled condition; and a selectively activable inflatable member adapted to be disposed in the space between the longitudinal shaft and the medical device, wherein in an activated state, the inflatable member expands radially relative to the shaft, thereby urging the at least one retention member to disengage from the at least one recess; and/or the activable inflatable member is an inflatable balloon; and/or the delivery system further comprises a lumen along the shaft for delivering a fluid to the activable inflatable member; and/or the retainer further comprises a plurality of recesses configured to receive a plurality of strut junctions of a stent of the medical device; and/or the inflatable element comprises a woven or braided polymer; and/or the delivery system further comprises an inflation medium to selectively activate the inflatable member; and/or the inflation medium comprises saline, air or helium; and/or the delivery system further comprises a sensor for detecting an engagement of the retention member with the corresponding recess; and/or the delivery system is configured to automatically activate the inflatable member responsive to a signal from the sensor indicative of engagement of the retention member with the corresponding recess; and/or the recess comprises a neck; and a disc-like end; and/or the retention member comprises a strut; and a disc-like end, wherein the disc-like end of the recess is configured to accommodate the disc-like end of the retention member, and wherein the neck is configured to accommodate the strut; and/or the neck is substantially smaller than the disc-like end of the retention member.

A delivery system for an implantable medical device comprises an implantable device having at least one retention member, a delivery device for releasably securing the implantable device thereto, the delivery device comprising an elongated shaft, an elongated sheath surrounding a portion of the shaft and slidable relative thereto in a longitudinal direction, a retainer coupled to the shaft and configured to be received within the sheath, the retainer having a portion thereof configured to releasably receive the at least one retention member of the implantable device, and a selectively inflatable member adapted to be disposed in a space between the shaft and the implantable device, wherein the at least one retention member is configured to be released upon inflation of the inflatable member; and/or the activable inflatable member is a balloon; and/or the delivery system further comprises a sensor for detecting an engagement of the retention member with the corresponding recess; and/or the delivery system is configured to automatically activate the inflatable member responsive to a signal from the sensor indicative of engagement of the retention member with the corresponding recess; and/or the inflatable element comprises a woven or braided polymer.

A method for delivering an implantable medical device having at least one retention member coupled to a stent thereof comprises positioning a delivery device comprising a retainer, the implantable medical device, a balloon element disposed underneath at least the stent at a predetermined location in a heart, the implantable medical device being in a collapsed state thereof with the retention member engaged with corresponding at least one recess in the retainer, unsheathing the receiving space to expose at least the stent portion of the implantable medical device, and causing the balloon element to expand to disengage the at least one retention member from the corresponding at least one recess in the retainer, if the at least one retention member remains engaged with the at least one corresponding recess after an expansion of the medical device from its collapsed state; and/or the device further comprises a sensor for detecting engagement of at least one retention member with the corresponding recess; and wherein the step of causing the balloon to expand is automatic responsive to a signal from the sensor, the signal indicative of the engagement of at least one retention member with the corresponding recess; and/or introducing an inflation medium into the balloon element to cause the balloon element to expand.

Although the present disclosure has described particular embodiments in which the catheter assembly is inserted into the patient via an introducer and through the apex of the heart (i.e., transapical insertion), it is to be understood that the disclosure contemplates embodiments in which the catheter assembly extends through a portion of the vasculature of the patient to reach the heart, for example, through a transfemoral or subclavian artery. In such embodiments, some of the device components may have to be oriented in a different direction to that described herein. For example, the disclosure contemplates embodiments in which the distal portion of the catheter assembly approaches the mitral valve from the upstream side as well as from the downstream side of the valve.

It will be appreciated that the various dependent claims and the features set forth therein can be combined in different ways than presented in the initial claims. It will also be appreciated that the features described in connection with individual embodiments may be shared with others of the described embodiments.

The invention claimed is:

1. A delivery system for an implantable medical device having retention member, the delivery system comprising:
   a shaft extending in a longitudinal direction;
   an elongated sheath surrounding the shaft, the sheath being slidable relative to the shaft in the longitudinal direction;
   a receiving space defined inside of the sheath and adapted to receive the medical device in an assembled condition;
   a retainer positioned at a first end of the space, the retainer having at least one recess adapted to receive the retention member of the medical device in the assembled condition;
   a sensor for detecting engagement of the retention member with the recess; and
   an inflatable member adapted to be disposed in the space between the shaft and the medical device, wherein
   the delivery system is configured to automatically expand the inflatable member responsive to a signal from the sensor indicative of engagement of the retention member with the recess and,
   the inflatable member is configured to expand radially relative to the shaft, thereby urging the retention member to disengage from the recess.

2. The delivery system of claim 1, wherein the inflatable member is an inflatable balloon.

3. The delivery system of claim 1, further comprising:
   a lumen along the shaft for delivering a fluid to the inflatable member.

4. The delivery system of claim 1, wherein the retainer further comprises a plurality of recesses configured to receive a plurality of strut junctions of a stent of the medical device.

5. The delivery system of claim 1, wherein the inflatable member comprises a woven or braided polymer.

6. The delivery system of claim 1, further comprising:
an inflation medium to selectively expand the inflatable member.

7. The delivery system of claim 6, wherein the inflation medium comprises saline, air or helium.

8. The delivery system of claim 1, wherein the recess comprises:
a neck; and
a disc-shaped end.

9. The delivery system of claim 8, wherein the retention member comprises:
a strut; and
a disc-shaped end, wherein
the disc-shaped end of the recess is configured to accommodate the disc-shaped end of the retention member, and
the neck is configured to accommodate the strut.

10. The delivery system of claim 9, wherein the neck has a substantially smaller tranverse cross-section than the disc-shaped end of the retention member.

11. A delivery system for an implantable medical device, the delivery system comprising:
an implantable device having retention member;
a delivery device for releasably securing the implantable device thereto, the delivery device comprising:
an elongated shaft;
an elongated sheath surrounding a portion of the shaft and slidable relative thereto in a longitudinal direction;
a retainer coupled to the shaft and configured to be received within the sheath, the retainer having a recess configured to releasably receive the retention member of the implantable device;
a sensor for detecting engagement of the retention member with the recess; and
an inflatable member adapted to be disposed in a space between the shaft and the implantable device, wherein
the delivery system is configured to automatically expand the inflatable member responsive to a signal from the sensor indicative of engagement of the retention member with the recess, and
the retention member is configured to be released upon inflation of the inflatable member.

12. The delivery system of claim 11, wherein the inflatable member is a balloon.

13. The delivery system of claim 11, wherein the inflatable member comprises a woven or braided polymer.

* * * * *